US012508364B1

(12) United States Patent
Constantin et al.

(10) Patent No.: US 12,508,364 B1
(45) Date of Patent: Dec. 30, 2025

(54) SYSTEMS AND METHODS FOR MEDICAL DEVICE SETTINGS INITIALIZATION AND ADAPTATION

(71) Applicant: Tandem Diabetes Care, Inc., San Diego, CA (US)

(72) Inventors: Alexandra E. Constantin, San Diego, CA (US); Alexander Trahan, San Diego, CA (US); Larry Fu, San Diego, CA (US); Zahra Yarmohammadi, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 765 days.

(21) Appl. No.: 17/896,492

(22) Filed: Aug. 26, 2022

Related U.S. Application Data

(60) Provisional application No. 63/239,081, filed on Aug. 31, 2021.

(51) Int. Cl.
*A61M 5/172* (2006.01)
*G16H 20/17* (2018.01)

(52) U.S. Cl.
CPC .......... *A61M 5/1723* (2013.01); *G16H 20/17* (2018.01); *A61M 2205/50* (2013.01)

(58) Field of Classification Search
None
See application file for complete search history.

(56) References Cited

U.S. PATENT DOCUMENTS

2007/0233050 A1* 10/2007 Wehba .................. G16H 20/17 604/890.1
2010/0064257 A1* 3/2010 Buck ...................... G16H 20/17 713/1

* cited by examiner

*Primary Examiner* — Manuel A Mendez
(74) *Attorney, Agent, or Firm* — Morgan, Lewis & Bockius LLP

(57) ABSTRACT

Systems and methods implement algorithms for initializing medical devices, including by programming initial medical device settings. Further, systems and methods implement adaptive algorithms for changing medical device settings. Settings initialization algorithms can calculate the settings most likely to be applicable for the patient at-issue using databases of positive clinical outcomes and respective therapy settings for existing users. Settings adaptation algorithm are configured to update medical device therapy settings at one or more intervals including based on databases of positive clinical outcomes and respective therapy settings for existing users.

17 Claims, 11 Drawing Sheets

SYSTEMS AND METHODS FOR MEDICAL DEVICE SETTINGS INITIALIZATION AND ADAPTATION

RELATED APPLICATION

The present application claims the benefit of U.S. Provisional Application No. 63/239,081, filed Aug. 31, 2021, which is hereby incorporated herein in its entirety by reference.

TECHNICAL FIELD

The present technology relates generally to medical devices and, more particularly, to systems and methods for initializing and adapting medical device settings.

BACKGROUND

In order to begin using certain medical devices, patients and/or their healthcare providers need to program the medical device with certain settings. For example, people with diabetes (PWDs) and/or their healthcare provider need to program the PWD user's insulin pump with therapy settings. Therapy settings can include basal rates by time of day (meant to keep glucose steady and at target when someone is not eating or engaging in physical activity), carb ratios (CRs) (used to calculate the amount of insulin someone should inject to cover a meal with a specific number of carbohydrates), insulin sensitivity factors (ISFs)/correction factors (used to calculate the amount of insulin someone needs to take to bring their blood glucose back to target when they are high), or other variables such as insulin action time, glucose target or target range, weight, total daily insulin dose, etc.

In the aforementioned insulin pump context, therapy settings can vary throughout the day, and each one can be set for intervals of time as short as 30 minutes throughout the day, including on multiple profiles. This gives rise to thousands of parameters that could be configured to get started on a pump. Further, therapy settings can include new and difficult terminology for PWDs, which can increase the difficulty of programming insulin pumps.

Today, healthcare providers provide initial settings as part of a pump start-up form. These settings are typically entered in the pump during the PWD initial pump training. Optimization of settings requires expert retrospective data analysis and is typically performed by healthcare providers a few times a year (e.g. every six months). During onboarding, people with diabetes require daily, then weekly, adjustments to achieve good clinical outcomes on a pump. Accordingly, in order to reach optimal settings, patients typically need several adjustments, often over a period of years.

Therefore, there is a need for systems and methods to automatically initialize and adapt medical device settings in order to reduce the burden of diabetes educators, increase time for holistic care, reduce knowledge needed to prescribe a pump, optimize glycemic outcomes, and improve the onboarding experience.

SUMMARY

Systems and methods of the present disclosure implement algorithms for initializing medical devices, including by programming initial medical device settings. Further, systems and methods of the present disclosure implement adaptive algorithms for changing medical device settings after initialization.

In an embodiment, a settings initialization algorithm is configured to set medical device therapy settings for initial use. For example, embodiments of settings initialization algorithms can calculate the settings most likely to be applicable for the patient at-issue using databases of positive clinical outcomes and respective therapy settings for existing users. In contrast to conventional solutions which typically rely on limited clinical study data, embodiments described herein utilize large data sets of optimized medical device settings known to be effective.

In an embodiment, a settings adaptation algorithm is configured to update medical device therapy settings at one or more intervals. For example, after identifying glucose readings influenced by each therapy setting, probabilities of glycemic outcomes compared to target outcomes can be used to update the settings. In embodiments, the one or more intervals can include regular intervals or irregular intervals. In an embodiment, small, frequent adjustments to therapy settings allow the medical device to reach optimal therapy settings safely and sooner than traditional methods of less frequent, larger adjustments to therapy settings. Further, certain medical devices are moving towards smaller form factors and thus smaller, limited resources (e.g., "patch pumps" and the like). Embodiments of the settings adaptation algorithm can be calculated incrementally (e.g., with every glucose value coming in). Accordingly, embodiments can allocate use of limited resources more efficiently than traditional adaptation algorithms and are better suited for limited resource devices.

In a feature and advantage of embodiments, distributions of settings for other user devices are utilized to select likely settings for the instant user. For example, values in the relative "middle" of certain distributions can be considered very likely, while values "outside" of certain distributions can be considered anomalous. Accordingly, utilizing setting values of similar users, certain other settings can be calculated or determined for the instant user.

In a feature and advantage of embodiments, the burden on diabetes educators is reduced in their support of the patient in using the pump, which increases time available for holistic care. Further, reduced pump support time allows diabetes educators to help additional patients.

In a feature and advantage of embodiments, the knowledge required of primary care providers to prescribe a medical device is reduced. Further, primary care providers are able to reduce their relative risk and responsibility when selecting therapy settings due to the reliability of the algorithms. Moreover, primary care providers are able to optimize patient outcomes.

In a feature and advantage of embodiments, medical device patients are provided increased access to the medical device. In particular, PWD that use embodiments have improved glycemic outcomes and improved device satisfaction. Further, the number of follow-up appointments is reduced, as well as the attrition rates.

In a feature and advantage of embodiments, various architectures are considered. For example, embodiments described herein can be implemented such that initialization and adaptation algorithms are implemented in the medical device. In other embodiments, the medical device is pre-programmed with certain settings using embodiments of the initialization and adaptation algorithms such that the algorithms themselves do not execute on the medical device, but rather, the resulting settings are programmed in the medical device. In further embodiments, the medical device can be communicatively coupled to a mobile device which can input additional data into the algorithms described herein; for example, the mobile device can communicate a user's exercise or how the pump is being used. In further embodiments, the medical device can be communicatively coupled to a server containing or operably coupled to a repository of patient population data. Accordingly, adaptation algorithms can be executed and additional adaptive settings can be pushed to the medical device based on the patient population data. Such embodiments therefore allow the user to utilize different profiles for contextual use (exercise, travel, changing of time zones, etc.). In certain embodiments, the medical device user can create such profiles. In other embodiments, profiles can be created and implemented based on the repository data.

In further embodiments, a user can access a web portal for decision support or recommendations, which can execute embodiments of the initialization or adaptation algorithms. In embodiments, the medical device can adapt to the user as it learns about the user and the context in which the medical device is used. One skilled in the art will appreciate that the aforementioned architectures can be readily interchanged such that various engines, algorithms, tools, etc. can be executed in a variety of physically realizable configurations or distributions among components.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1:
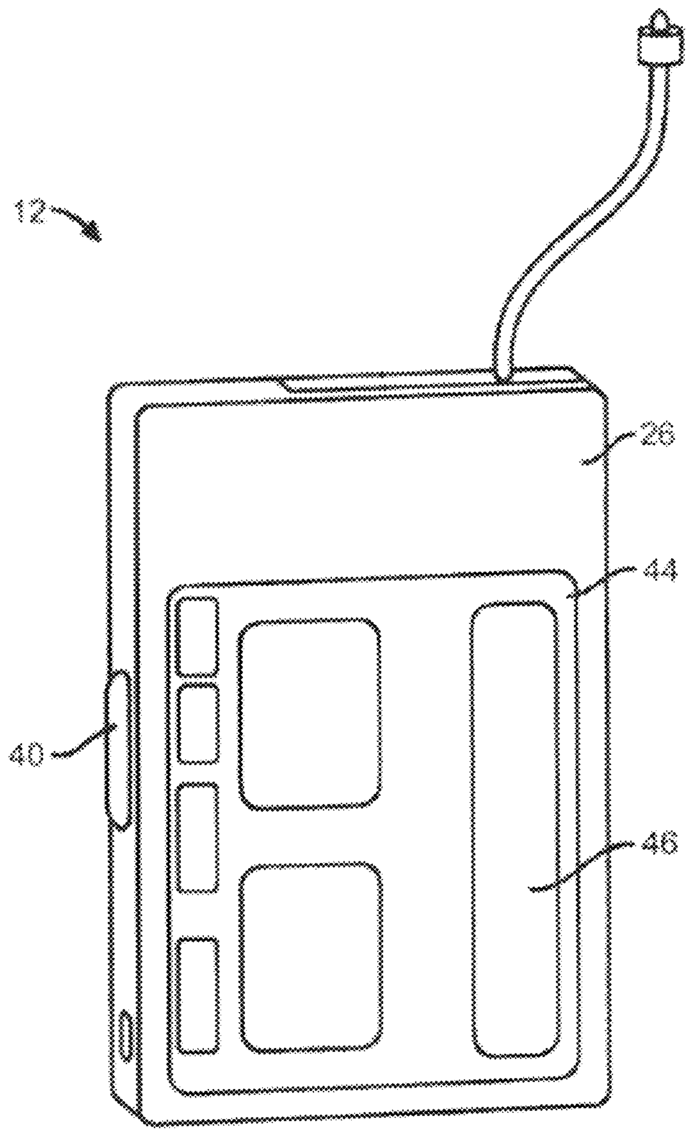
FIG. 1 is a perspective view of an ambulatory infusion pump for use with embodiments of the disclosure.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Referring to FIG. 1, a block diagram of an ambulatory infusion pump 12 for use with embodiments of the disclosure is depicted. Pump 12 includes a pumping or delivery mechanism and reservoir for delivering insulin or other medicament to a patient and an output/display 44. Output/display 44 can include an interactive and/or touch sensitive screen 46 having an input device such as, for example, a touch screen comprising a capacitive screen or a resistive screen. Pump 12 may additionally or instead include one or more of a keyboard, a microphone or other input devices known in the art for data entry, some or all of which may be separate from the display. Pump 12 can also include a capability to operatively couple to one or more other display devices such as a remote display (e.g., a dedicated remote display or a Continuous Glucose Monitor (CGM) display), a remote control device, or a consumer electronic device (e.g., laptop computer, personal computer, tablet computer, smartphone, electronic watch, electronic health or fitness monitor, or personal digital assistant). Further details regarding such pump devices can be found in U.S. Pat. No. 8,287,495, which is herein incorporated by reference. It is to be appreciated that pump 12 can be optionally configured to deliver one or more additional or other medicaments to a patient.

Figure 2:
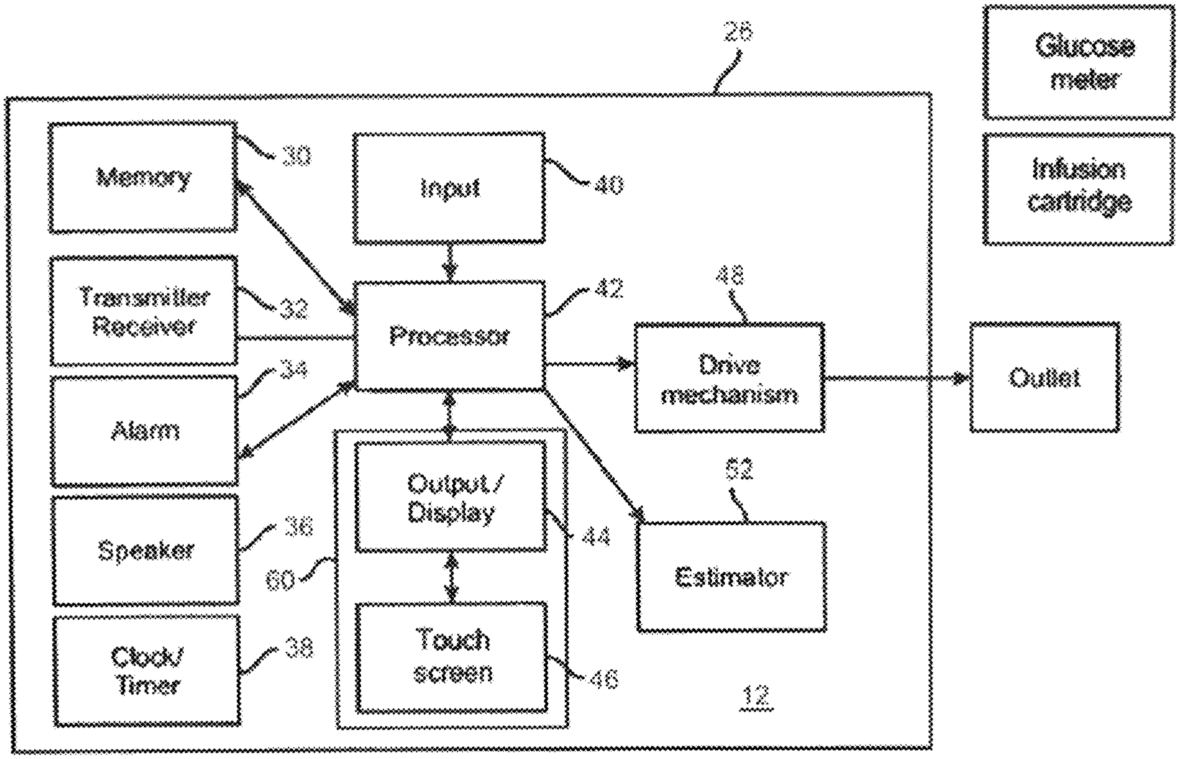
FIG. 2 is a block diagram of the ambulatory infusion pump of FIG. 1, according to an embodiment.

Referring to FIG. 2, a block diagram of ambulatory infusion pump 12 of FIG. 1 is depicted, according to an embodiment. More particularly, FIG. 2 depicts a block diagram of some of the features that may be included within housing 26 of pump 12. Pump 12 can include a processor 42 that controls the overall functions of the pump. Pump 12 cab also include, e.g., a memory device 30, a transmitter/receiver 32, an alarm 34, a speaker 36, a clock/timer 38, an input device 40, a user interface suitable for accepting input and commands from a user such as a caregiver or patient, a drive mechanism 48, an estimator device 52 and a microphone (not pictured). One embodiment of a user interface is a graphical user interface (GUI) 60 having a touch sensitive screen 46 with input capability. In some embodiments, processor 42 can communicate with one or more other processors within pump 12 and/or one or more processors of other devices through transmitter/receiver 32 such as a remote device (e.g., CGM device), a remote control device, server device, or a consumer electronic device (e.g., laptop computer, personal computer, tablet computer, smartphone, electronic watch, electronic health or fitness monitor, or personal digital assistant). In some embodiments, the communication is effectuated wirelessly, by way of example only, via a near field communication (NFC) radio frequency (RF) transmitter or a transmitter operating according to a "Wi-Fi" or Bluetooth® protocol, Bluetooth® low energy protocol or the like. Processor 42 can also include programming to receive signals and/or other data from an input device, such as, by way of example, a pressure sensor, a temperature sensor, or the like.

Figure 3:
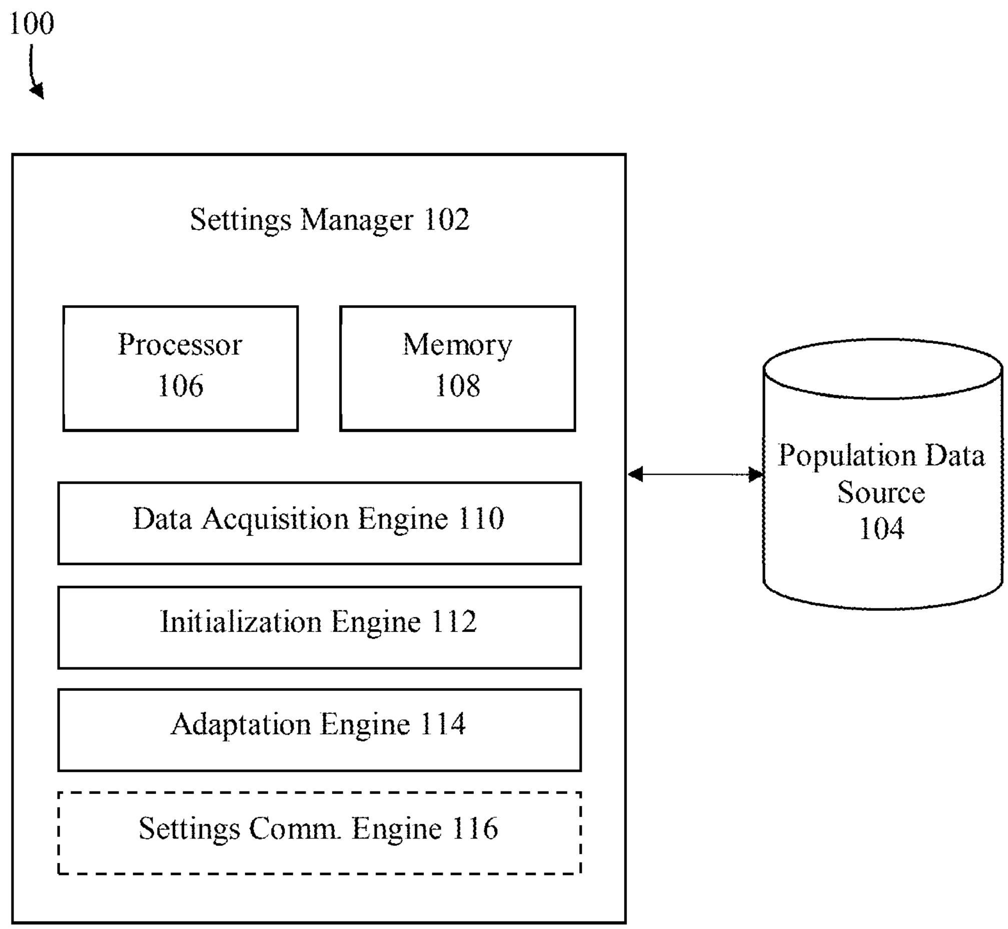
FIG. 3 is a block diagram of a system for managing medical device settings, according to an embodiment.

Referring to FIG. 3, a block diagram of a system 100 for managing medical device settings is depicted, according to an embodiment. System 100 generally comprises a settings manager 102 and a population data source 104.

Some of the subsystems of system 100 include various engines or tools, each of which is constructed, programmed, configured, or otherwise adapted, to autonomously carry out a function or set of functions. The term engine as used herein is defined as a real-world device, component, or arrangement of components implemented using hardware, such as by an application specific integrated circuit (ASIC) or field-programmable gate array (FPGA), for example, or as a combination of hardware and software, such as by a microprocessor system and a set of program instructions that adapt the engine to implement the particular functionality, which (while being executed) transform the microprocessor system into a special-purpose device. An engine can also be implemented as a combination of the two, with certain functions facilitated by hardware alone, and other functions facilitated by a combination of hardware and software. In certain implementations, at least a portion, and in some cases, all, of an engine can be executed on the processor(s) of one or more computing platforms that are made up of hardware (e.g., one or more processors, data storage devices such as memory or drive storage, input/output facilities such as network interface devices, video devices, keyboard, mouse or touchscreen devices, etc.) that execute an operating system, system programs, and application programs, while also implementing the engine using multitasking, multithreading, distributed (e.g., cluster, peer-peer, cloud, etc.) processing where appropriate, or other such techniques. Accordingly, each engine can be realized in a variety of physically realizable configurations, and should generally not be limited to any particular implementation exemplified herein, unless such limitations are expressly called out. In addition, an engine can itself be composed of more than one sub-engines, each of which can be regarded as an engine in its own right. Moreover, in the embodiments described herein, each of the various engines corresponds to a defined autonomous functionality; however, it should be understood that in other contemplated embodiments, each functionality can be distributed to more than one engine. Likewise, in other contemplated embodiments, multiple defined functionalities may be implemented by a single engine that performs those multiple functions, possibly alongside other functions, or distributed differently among a set of engines than specifically illustrated in the examples herein.

Settings manager 102 generally comprises a processor 106 and a memory 108, and a plurality of engines configured to execute on processor 106, such as a data acquisition engine 110, an initialization engine 112, an adaptation engine 114, and optionally, a settings communication engine 116, as depicted in FIG. 3.

The engines of settings manager 102 are depicted on a single device for ease of explanation. However, as will be readily understood by one of ordinary skill in the art, and as will be described further below with respect to FIG. 4, the engines of settings manager 102 can be implemented on several servers, device, clouds, or networks. For example, settings manager 102 can itself be implemented on a medical device, such as ambulatory infusion pump 12. In other embodiments, settings manager 102 can be implemented on a device separate from ambulatory infusion pump 12 such as a networked computing device or networked server. In still other embodiments, portions of settings manager 102 can be implemented on the medical device and portions can be implemented on a separate device.

Population data source 104 comprises a store of historical medical device data. For example, historical medical device data can include data from existing medical devices, such as medical device settings (as inputs that generate an outcome) and the resulting glucose data (outcome). In an embodiment, population data source 104 comprises a SQL database of cleaned and processed data from a patient population having positive clinical outcomes. In embodiments, population data source 104 can be implemented as a general purpose database management storage system (DBMS) or relational DBMS as implemented by, for example, Oracle, IBM DB2, Microsoft SQL Server, PostgreSQL, MySQL, SQLite, Linux, or Unix solutions.

Referring again to settings manager 102, processor 106 can be any programmable device that accepts digital data as input, is configured to process the input according to instructions or algorithms, and provides results as outputs. In an embodiment, processor 106 can be a central processing unit (CPU) configured to carry out the instructions of a computer program. Processor 106 is therefore configured to perform at least basic arithmetical, logical, and input/output operations.

Memory 108 can comprise volatile or non-volatile memory as required by the coupled processor 106 to not only provide space to execute the instructions or algorithms, but to provide the space to store the instructions themselves. In embodiments, volatile memory can include random access memory (RAM), dynamic random access memory (DRAM), or static random access memory (SRAM), for example. In embodiments, non-volatile memory can include read-only memory, flash memory, ferroelectric RAM, hard disk, floppy disk, magnetic tape, or optical disc storage, for example. The foregoing lists in no way limit the type of memory that can be used, as these embodiments are given only by way of example and are not intended to limit the scope of embodiments.

Data acquisition engine 110 is configured to interface with population data source 104. In particular, data acquisition engine 110 can read and/or receive data from population data source 104. In an embodiment, data acquisition engine 110 is configured to store data received from population data source 104 in memory 108. In other embodiments, data acquisition engine 110 can be configured to store data received from population data source 104 in its own DBMS structure.

Initialization engine 112 is configured to execute a function or set of functions to determine initial therapy settings for a medical device based on data analyzed from population data source 104. In embodiments, initialization engine 112 can be further configured to determine initial therapy settings based on user-specific data. In embodiments, initialization engine 112 can be further configured to determine initial therapy settings based on the context in which the medical device is used.

Adaptation engine 114 is configured to execute a function or set of functions to determine or adapt a medical device from initial (or existing) settings to different therapy settings based on data analyzed from population data source 104. In embodiments, adaptation engine 114 can be further configured to determine or adapt medical device settings based on user-specific data. In embodiments, adaptation engine 114 can be further configured to determine or adapt medical device settings based on the context in which the medical device is used.

Settings communication engine 116 is configured to execute a function or set of functions to communicate such settings to a medical device or otherwise program the medical device with initial or adapted therapy settings. For example, in an embodiment where settings manager 102 is not on a medical device, settings communication engine 116 can communicate with the medical device to configure the appropriate settings.

In general operation, initialization engine 112 can command data acquisition engine 110 to read or receive data from population data source 104. Initialization engine 112 can perform certain calculations, distributions, analyzation, or other appropriate determinations on data received by data acquisition engine 110 as well as other data received related to the medical device or patient to program initial setting values for the medical device. Settings communication engine 116 can communicate with or otherwise program the medical device with the initial setting values.

Once the medical device is initialized, adaptation engine can analyze data from the medical device (e.g., using settings communication engine 116) and data from population data source 104 (e.g., using data acquisition engine 110) to adapt the existing setting values to adapted setting values. Similarly, settings communication engine 116 can communicate with or otherwise program the medical device with the adapted setting values.

Figure 4:
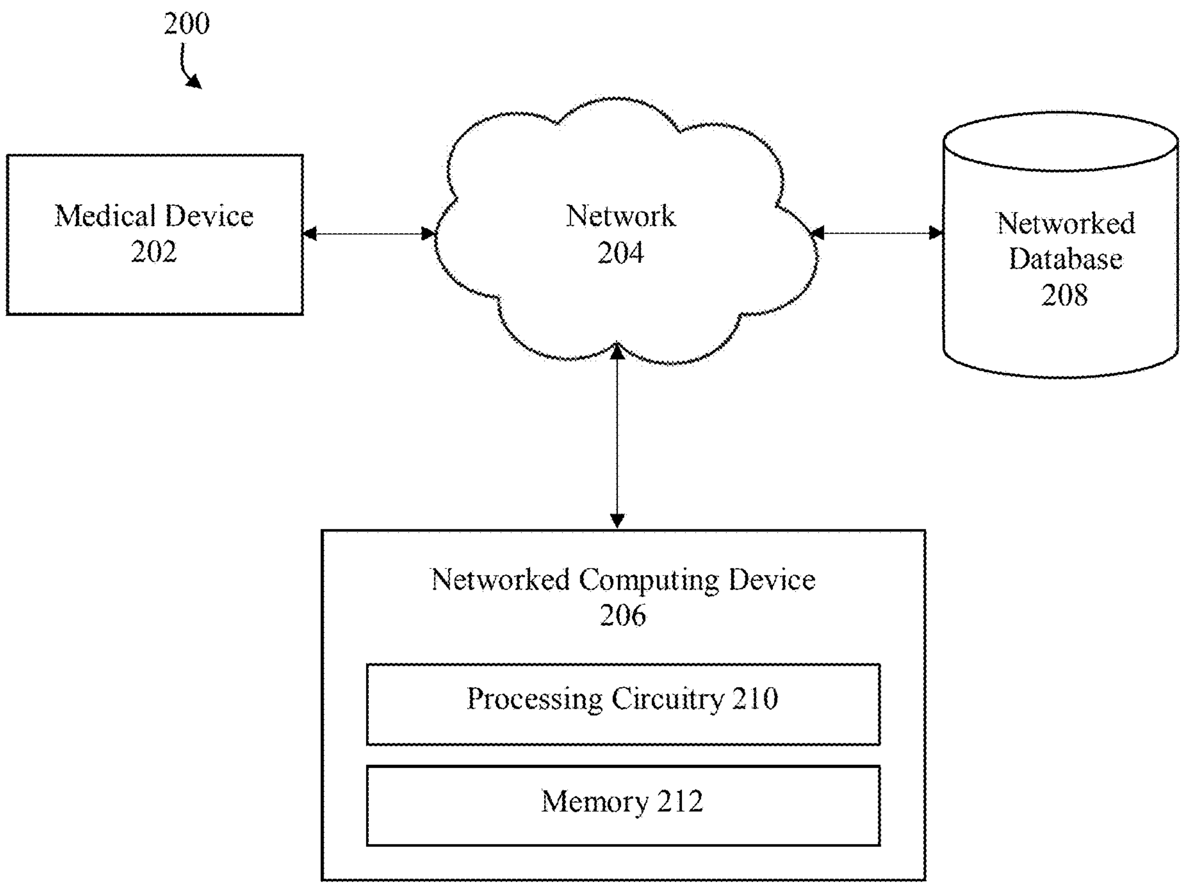
FIG. 4 is a block diagram of a system for managing medical device settings, according to an embodiment.

Referring to FIG. 4, a block diagram of a system 200 for managing medical device settings is depicted, according to an embodiment. System 200 generally comprises a medical device 202, a network 204, a networked computing device 206, and a networked database 208.

With reference to medical device 202, network 204, networked computing device 206, and networked database 208, embodiments of and the corresponding methods of initializing and adapting medical device 202 settings can be performed in cloud computing, client-server, or other networked environment, or any combination thereof. The components of the system can be located in a singular "cloud" or network, or spread among many clouds or networks. End-user knowledge of the physical location and configuration of components of the system is not required.

Medical device 202 comprises any medical device requiring therapy settings. For example, medical device 202 can be ambulatory infusion pump 12. Medical device could alternatively or additionally include a smart insulin pen, continuous glucose monitor, medical device application operating on a smartphone or other device alone or in a system in combination with one or more of each other and/or an ambulatory infusion pump. Such devices could be operated in open loop mode, closed loop mode, or with discrete injections.

Network 204 comprises a communication network for connecting the components of system 200. In an embodiment, network 204 can include a wireless communication network, a wired communication network, a cellular communication network, the Internet, and/or a short-range radio network (e.g., via Bluetooth).

Networked computing device 206 comprises processing circuitry 210 and memory 212. Processing circuitry 210 can include one or more processors that are configured to implement functionality and/or process instructions for execution within networked computing device 206. For example, processing circuitry 210 can be capable of processing instructions stored in memory 212. Processing circuitry 210 can include, for example, microprocessors, DSPs, ASICs, FPGAs, or equivalent discrete or integrated logic circuitry, or a combination of any of the foregoing devices or circuitry. Accordingly, processing circuitry 210 can include any suitable structure, whether in hardware, software, firmware, or any combination thereof, to perform the functions ascribed herein to processing circuitry 210.

Memory 212 can be configured to store information within networked computing device 206 during operation. Memory 212 can include a computer-readable storage medium or computer-readable storage device. In some examples, memory 212 includes one or more of a short-term memory or a long-term memory. Memory 212 can include, for example, RAM, dynamic random access memories (DRAM), static random access memories (SRAM), magnetic discs, optical discs, flash memories, or forms of electrically programmable memories (EPROM) or EEPROM. In some examples, memory 212 is used to store data indicative of instructions for execution by processing circuitry 210. Memory 212 can be used by software or applications running on external networked computing device 206 to temporarily store information during program execution.

Networked database 208 comprises a database of medical device data. For example, networked database 208 can be a store of historical medical device data of settings and outcomes, such as population data source 104.

Referring also to FIG. 3, settings manager 102 can be implemented on medical device 202. In other embodiments, settings manager 102 can be implemented on networked computing device 206. In still other embodiments, portions of settings manager 102 can be implemented on medical device 202 and other portions can be implemented on networked computing device 206.

Figure 5:
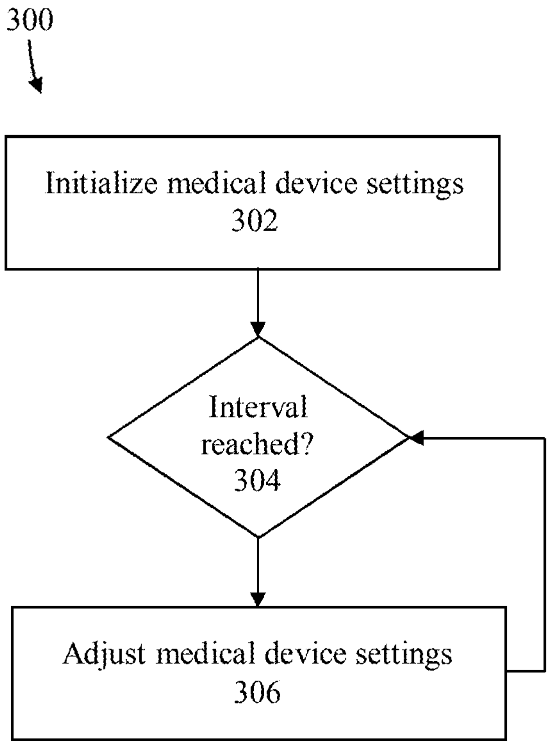
FIG. 5 is a flowchart of a method for managing medical device settings, according to an embodiment.

Referring to FIG. 5, a flowchart of a method 300 for managing medical device settings is depicted, according to an embodiment. Method 300 can be implemented by the aforementioned devices and systems, such as ambulatory infusion pump 12 or other medical device or medical device system, system 100, and/or system 200.

At 302, initial medical device settings are determined and programmed into the medical device. For example, referring to FIG. 3, initialization engine 112 can determine appropriate initial medical device settings, which can be programmed into medical device 202. In an embodiment in which settings manager 102 is implemented on medical device 202, medical device 202 can program the initial medical device settings calculated by initialization engine 112 itself. In another embodiment in which portions (or all) of settings manager 102 outside of medical device 202, networked computing device 206 can utilize settings communication engine 116 to transmit the determined initial medical device settings to medical device 202.

At 304, method 300 determines if an adjustment interval is reached in order to adjust medical device 202 settings. For example, adaptation engine 114 can check at one or more intervals whether medical device 202 settings are to be updated. In embodiments, the one or more intervals can include regular intervals or irregular intervals. Such intervals can be predetermined or preprogrammed and/or set or updated as needed. For example, an interval between 1 day and 1 week can be utilized.

At 306, updated medical device settings are determined and programmed into the medical device. For example, adaptation engine 114 can determine appropriate updated medical device settings, which can be programmed into medical device 202.

Accordingly, embodiments provide automatically updated medical device settings without the need for provider or user (e.g., PWD) review and input. Such embodiments are described herein as example cloud-based implementations, pump-exclusive and/or other medical device (e.g., smart pen or medical device system) implementations, and cloud-pump hybrid implementations. The automatically updated settings can be optional or required, visible or invisible to the user, overridable or non-overridable, or requiring HCP approval or not requiring HCP approval.

In other embodiments, recommended settings can be provided such that the settings can subsequently programmed or accepted by a user (HCP or PWD). For example, networked computing device 206 can be utilized for decision support for HCPs and/or PWDs. Suggested changes based on the described algorithms can suggest changes but require manual input to update the settings. In an embodiment, networked computing device 206 can be a tool operably coupled to medical device 202 to receive data but not configured to program medical device 202 such that HCPs and/or PWDs can access networked computing device 206 for recommended settings before taking other steps to implement such settings on medical device 202. In other embodiments, networked computing device 206 can further comprise a calculator configured to push settings to medical device 202.

Figure 6:
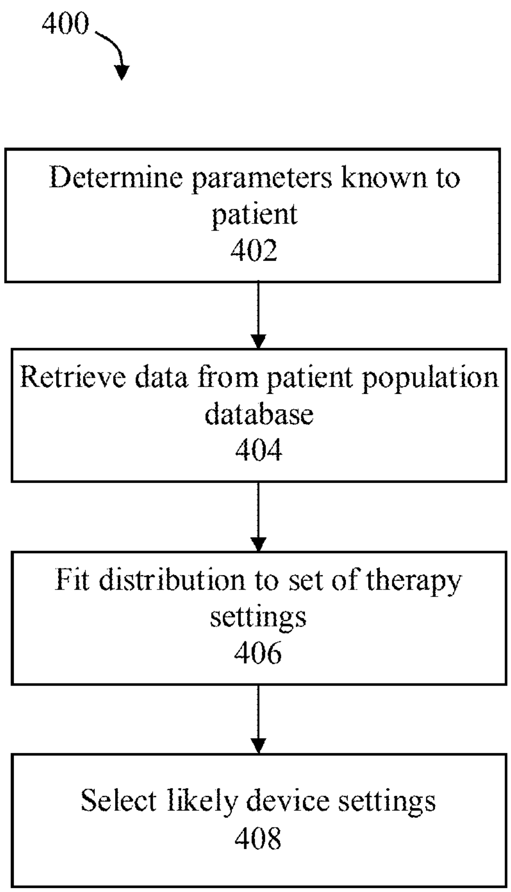
FIG. 6 is a flowchart of a method for initializing medical device settings, according to an embodiment.

Referring to FIG. 6, a flowchart of a method 400 for initializing medical device settings is depicted, according to an embodiment. Method 400 can be implemented by, for example, initialization engine 112.

Method 400 generally comprises at 402, determining parameters known to the patient. For example, an individual's basal needs, carb ratios, and insulin sensitivity factors are highly correlated with the patient's age, weight, total daily insulin needs, and meal sizes. In fact, these variables follow multivariate log-normal distributions that can be used to initialize some of the settings to the most likely settings given the parameters or device settings that are known.

Typically, a person who onboards to a pump from multiple daily injections knows their long-acting dose (which can be directly converted to a basal rate by dividing by 24 hours). Age and weight are also commonly known parameters, and total daily insulin is sometimes preferred by HCPs but more difficult to calculate unless a user has a digital pen. Accordingly, known parameters are determined, such as by user input or HCP input.

At 404, data is received from a patient population database, including existing medical device settings and the respective outcome of those settings for other patients.

At 406, one or more distributions are fit to a set of therapy settings based on the data from the patient population database.

At 408, likely device settings are selected based on the one or more distributions of 406. In embodiments, data from the patient population database for patients that share known parameters with the user can be weighted more heavily than data from patients that do not share known parameters with the user.

For example, referring to 404-408, therapy settings combinations (Total Daily Dose, Total Daily Basal Dose (TDBD)-insulin required to cover daily basal requirement (u/day), CR, ISF, etc.) from current and historical pump users can be utilized from patient population database(s) at 404. In an embodiment, multivariate log normal distribution represents this data well. Fitting a distribution to combinations of therapy settings and other features allows the selection of the most likely value for unknown settings based on the values of known settings. Fitting different distributions for different populations of interest (e.g., People with Type 1 diabetes vs people with Type 2 diabetes; pediatrics vs. adolescents vs. adults) can also result in more accurate settings.

Figure 7A:
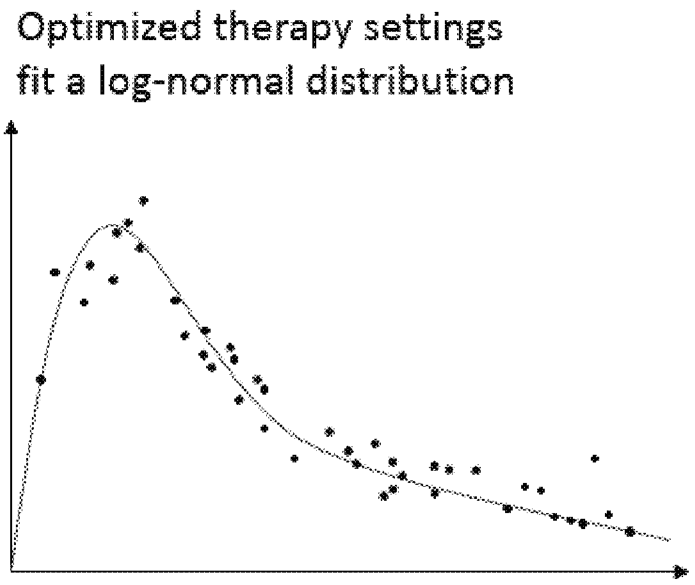
FIG. 7A is a graph of optimized therapy settings fit to a log-normal distribution, according to an embodiment.
Figure 7B:
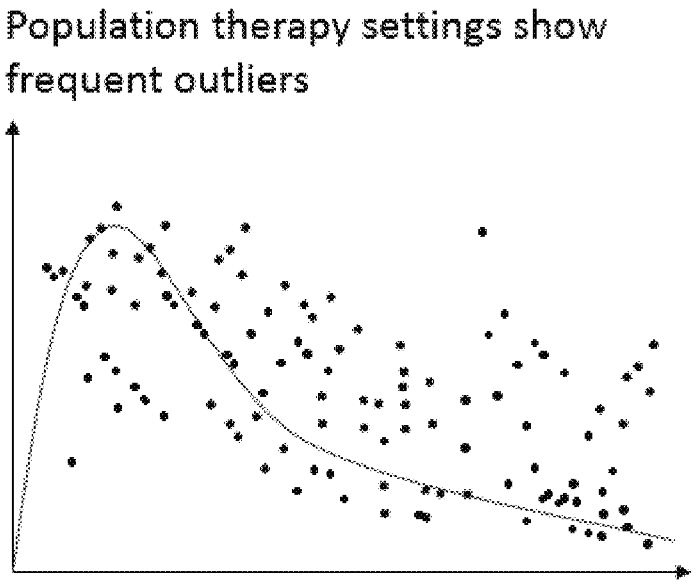
FIG. 7B is a graph of a population of therapy settings illustrating frequent outliers, according to an embodiment.

Referring further to FIG. 7A, a graph of optimized therapy settings fit to a log-normal distribution is depicted, according to an embodiment. As described herein, therapy settings can include TDBD, CR, ISF fit along the distribution depicted. Further, referring to FIG. 7B, a graph of a population of therapy settings illustrating frequent outliers is depicted, according to an embodiment. Accordingly, submethods for identifying a subgroup of settings using another known subgroup are described below, such as at 406.

Fitting a multivariate log normal distribution to a set of therapy settings, such as (TDI, CR, ISF, TDBD), yields a normal distribution for the log-transformed settings, $x \sim \mathcal{N}(\mu, \Sigma)$. Values TDBD, CR and ISF can then be selected to maximize the log-likelihood of the observed TDI, such that:

$$\begin{bmatrix} CR \\ ISF \end{bmatrix}_{expected} = \text{Argmax}\left[\ell\left(\begin{bmatrix} CR \\ ISF \end{bmatrix} \middle| TDBD\right)\right]$$

In practice, the distribution $x \sim \mathcal{N}(\mu, \Sigma)$ can be used to create a conditional distribution, which can then be used to find the most likely values for unknown variables (i.e., TDBD, CR and ISF), given some subset of variables (i.e., TDI). This can be shown by splitting the n-dimensional random vector into known ($x_1$) and unknown ($x_2$) segments:

$$x = \begin{bmatrix} x_1 \\ x_2 \end{bmatrix},$$

such that the dimensions of $x_1$ and $x_2$ sum to n.

This has a normal distribution $\mathcal{N}(x, \mu, \Sigma)$ with $$\mu = \begin{bmatrix} \mu_1 \\ \mu_2 \end{bmatrix}; \sum = \begin{bmatrix} \sum_{11} & \sum_{12} \\ \sum_{21} & \sum_{22} \end{bmatrix}.$$

Note that $\Sigma = \Sigma^T$ and $$\sum_{21} = \sum_{21}^{T}.$$

Accordingly, expected value and covariance equations can be reduced such that most likely settings for a known TDI and can be used to select initial settings for new pump users (at 408).

Figure 8:
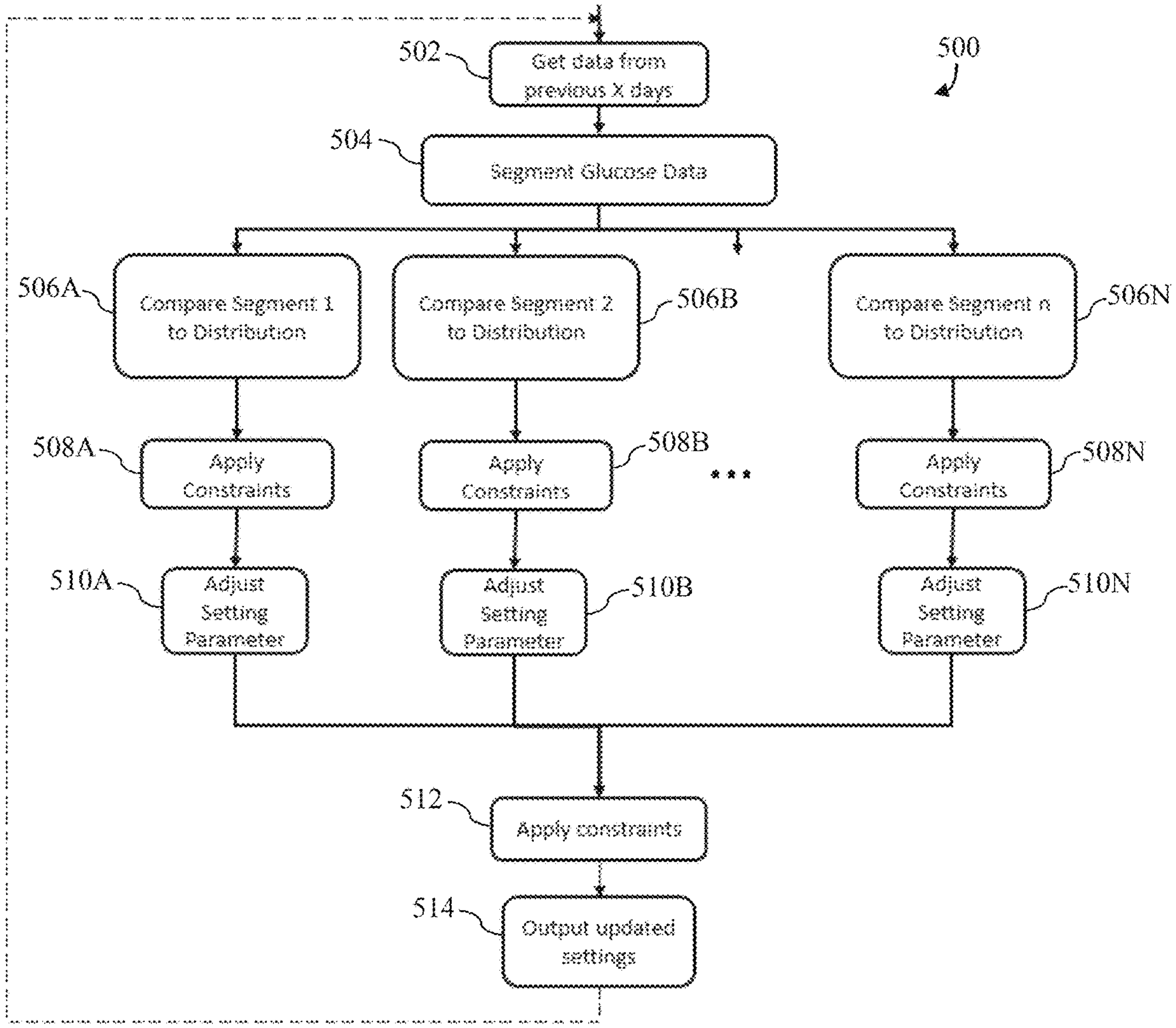
FIG. 8 is a flowchart of a method for adapting medical device settings, according to an embodiment.

Referring to FIG. 8, a flowchart of a method 500 for adapting medical device settings is depicted, according to an embodiment. Method 500 can be implemented by, for example, adaptation engine 114.

In general, embodiments are used to update the therapy settings for a medical device based on data from a certain number of previous days. For example, at 502, data from a previous number X days is retrieved. In an embodiment, the previous one to seven days are utilized, using the largest period from the most recent upload back to the most recent settings change (or seven days, whichever is smaller). In some embodiments, there is less than 1 day of data, no recommendation will be provided (though not depicted in FIG. 8). In other embodiments, recommendations can be provided more frequently such that a full day of data is not needed For example, if the most recent upload was 1 day ago and the most recent settings change was 4 days ago, data between 1-4 days ago would be analyzed. If the most recent settings change was 14 days ago (greater than 7 days), data between 1-8 days ago would be used. If settings had been changed 1.5 days ago, no recommendation would be provided since there would be less than 24 hours of data to analyze.

At 504, these data are divided into segments where each setting has the most influence, and those segments are used to generate recommended adjustments to their respective settings. In particular, glucose data is split into the most likely cause (e.g., Basal, CR, ISF). For example, referring to 506A, a mismatch is utilized. In an embodiment, a given segment (e.g., Segment 1 as in 504A) can be compared to an expected value based on a distribution for that segment. Similarly, mismatches can be calculated for the other segments (Segment 2 at 506B through Segment n at 506N). The probability distribution for a segment can be used to compare the target glycemic outcomes to the actual glycemic outcomes observed. If there is a mismatch, the parameters for that segment can be adjusted.

At 508A, an adjustment is calculated according to one or more constraints. In an embodiment, if the adjusted value is outside of certain defined values or percentages, (e.g., less than a predetermined value or percentage or greater than a predetermined value or percentage, the adjusted value can be constrained. Similarly, adjustments can be calculated and constrained for the other segments (Segment 2 at 508B through Segment n at 508N).

At 510A, the adjusted setting parameter is determined according to the constraint. Similarly, adjusted setting parameters can be determined according to respective constraints for the other segments (Segment 2 at 510B through Segment n at 510N).

At 512, overall constraints can be applied, and at 514, updated settings are generated as a result of the constraints. As depicted throughout method 500, limits and constraints are used to ensure the recommendations are gradual and feasible. The updated settings can then be programmed into the medical device. In embodiments, as depicted in FIG. 8, method 500 can optionally further use the updated settings as an input in another iteration or instance of method 500.

In an embodiment, adaptation engine 114 can make settings recommendations based on a representative group of therapy settings from the recommendation period. If a user has multiple groups of therapy settings during the period, the multiple groups can be condensed into one group to use as a baseline.

To decide on a condensed group of therapy settings for each user, embodiments check the user's historical data to pick the most used profile as a primary profile. Users can define multiple therapy settings profiles and may switch between multiple profiles over time. The algorithm reviews all profiles and selects the profile with the longest cumulative activation record (i.e., the most-used profile) as the primary profile. In other embodiments, the algorithm can adjust the settings of each profile based on the data corresponding to that profile.

In addition, each profile can consist of multiple segments. Every segment is a group of therapy settings associated with certain times of a day. During a day, the pump automatically shifts between segments based on each segment's starting time. Embodiments can track segment modifications associated with the primary profile to choose the most recent segment change. If the most recent change to the primary profile led to multiple segments, embodiments select the therapy settings with the lowest insulin delivery—the lowest basal rate (BR), highest carb ratio (CR), and highest insulin sensitivity factor (ISF)—along with the average target blood glucose from the pool of segments. This condensed group of settings is used as the recommendation baseline for each user. Finally, embodiments check if the condensed therapy settings are less than a minimum threshold (e.g., BR less than 0.5 u/hr), and if the values are below the threshold, embodiments issue a low therapy settings warning.

In an embodiment, adaptation engine 114 can update therapy settings at regular intervals. In an embodiment, a default update interval is 1 day where the algorithm runs every day and analyzes data from the previous day. However, other intervals are possible, as will be readily understood by one of ordinary skill in art the as described herein.

In a particular embodiment, the algorithm starts by identifying glucose readings influenced by each settings (basal, CR, or ISF). Glucose values are split into 4 subsets: glucose during times basal is the only insulin active, glucose after boluses with a meal components, glucose after correction boluses, and all glucose readings in the current update interval.

Glucose values follow a log-normal distribution. For each set of glucose values identified as described above, the parameters of the log-normal distribution are fit:

$$X \sim \text{Log normal}(\mu,\sigma)$$

which is equivalent to $$Y = \text{Log}(X) \sim \text{Normal}(\mu,\sigma)$$

and $\mu^* = \exp(\mu)$ and $\sigma^* = \exp(\sigma)$ are the geometric mean and standard deviation.

The log normal distribution can be used to set a constraint on the amount of time spent under a specific glucose level (thus limiting the probability of hypoglycemia). The algorithm assumes that glucose variability will remain unchanged before and after a settings change, and finds the preferred mean that would restrict the probability of going below a certain glucose threshold to a constant percentage. Thus, $\mu_{preferred}$ is found such that:

$$P(X<x)=p$$

where x is the glucose threshold and p is the desired probability.

In an embodiment, certain constraints are predefined. For example, the incidence of hypoglycemia is limited to 2%, and the time spent under a glucose target, such as, for example, 110 mg/dL is limited to 10%:

$$\mu^*_{preferred} = \max\left(70*(\sigma^*)^{-\sqrt{2}erf^{-1}(2+0.02-1)}, 110*(\sigma^*)^{-\sqrt{2}erf^{-1}(2+0.1-1)}\right)$$

In embodiment, such values can be set by the user.

A mismatch for each setting is calculated using the ratio between the desired and actual glucose geometric mean for glucose data corresponding to that setting, accounting for the proportional or inversely proportional relationship between the settings and mean glucose.

If the current glucose geometric mean is higher than preferred, then the basal rate needs to be increased, or the carb ratio or ISF need to be decreased respectively, which leads to taking more insulin. If the current glucose geometric mean is lower than preferred, then the basal rate needs to be decreased, or the carb ratio or ISF need to be increased respectively, which leads to taking less insulin.

The mismatch values are constrained to a percentage change to avoid drastic changes in a single update. For example, in a 5% constraint, a total daily basal dose (TDBD) mismatch of 1.18 would be converted to 1.05, and the updated TDBD would be 105% of the previous TDBD. A CR mismatch of 0.84 would be converted to 0.95, and the updated CR would be 95% of the previous CR. Settings with mismatches between 0.95 and 1.05 are left unchanged.

In embodiments, mismatch values can be constrained by larger change percentage constraints initially, with gradual decreases in the change percentage constraint over time (compared to, e.g., a 5% constraint throughout). Embodiments therefore result in bigger initial changes and smaller changes over time.

In certain embodiments, proposed ISF changes will be ignored to avoid updating multiple settings that will change glucose too much in the same direction. For example, logic can be included such that if TDBD is increased and CR is changed (increased or decreased), ISF is not changed. In another example, if TDBD is decreased and CR is changed, ISF is not decreased.

The same or similar algorithms can also be applied for specific diurnal segments (e.g., for each hour of a 24-hour day), changing the basal rate, ISF, and CR for 1-2 hours prior to the observed glucose values in order to get the desired settings profiles (this is due to the delay in insulin action for current rapid acting insulin).

Embodiments further account for hypoglycemic treatments by overriding the recommendations if too many hypoglycemic events occur. For example, a hypoglycemic event starts when glucose<70 mg/dL or a relevant alert is detected. The predictive hypoglycemic event triggers when, for example, the CGM alert triggers when CGM glucose reading is low. The end of an event occurs when both glucose>77 mg/dL and gPred30>77 mg/dL.

TDBD is overridden with a 5% decrease if there are more than three hypoglycemic events during the basal period days. If more than 50% of announced carb events (meals) correspond to hypoglycemic events, CR is overridden with a 5% increase. In an embodiment, if TDBD is overridden, CR is not changed.

Figure 9:
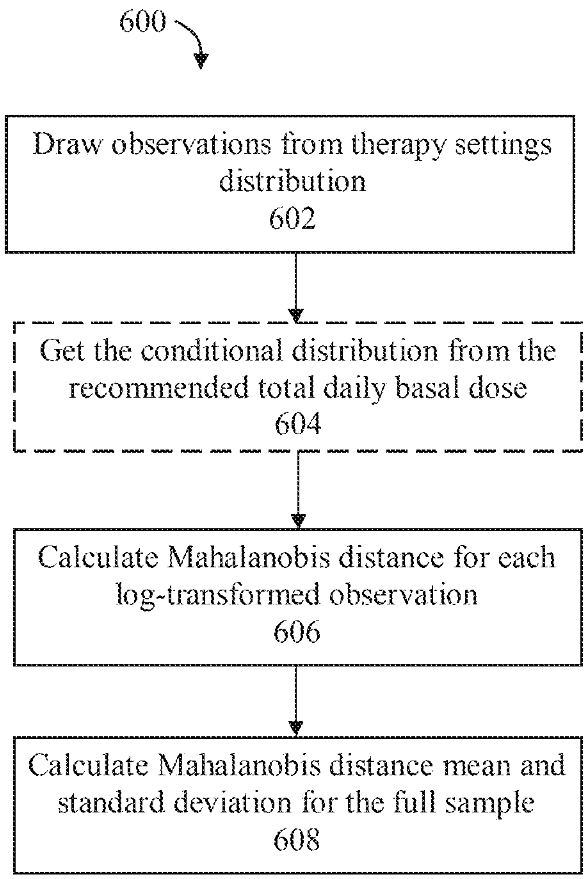
FIG. 9 is a flowchart of a method for generating a constraint for adaptation of medical device settings, according to an embodiment.

Referring to FIG. 9, a flowchart of a method 600 for generating a constraint for adaptation of medical device settings is depicted, according to an embodiment. In particular, settings can be further refined using Mahalanobis distance and distribution. Embodiments therefore implement a safety constraint meant to prevent scenarios where an error in one parameter is compensated for with an error in another parameter, and the relationship between the parameters becomes physiologically unlikely.

As illustrated, Mahalanobis distance and distribution are depicted to express the concept of measuring a distance from a point to a distribution in order to ascertain whether the point belongs to the distribution or not. Other multivariate analysis can also be used, as one will be readily appreciated by one of ordinary skill in the art.

At 602, a certain number of observations are determined from a therapy settings distribution. For example, 1000 observations can be determined, in an embodiment. Other numbers of observations can be utilized.

At 604, the conditional distribution is determined from the recommended total daily dose. For example, $\mathcal{N}$ (TBDB, CR, ISF|TDI) is calculated using the recommended TDI. In certain embodiments, 604 is conditional. In embodiments, 604 can be run once in advance.

At 606, a Mahalanobis distance is calculated for each log-transformed observation. For example, the Mahalanobis distance can be calculated for log-transformed CR and ISF observations.

At 608, the Mahalanobis distance mean and standard deviations are calculated for the full sample. An output of method 600 can include the Mahalanobis distance mean and Mahalanobis distance standard deviations.

Figure 10:
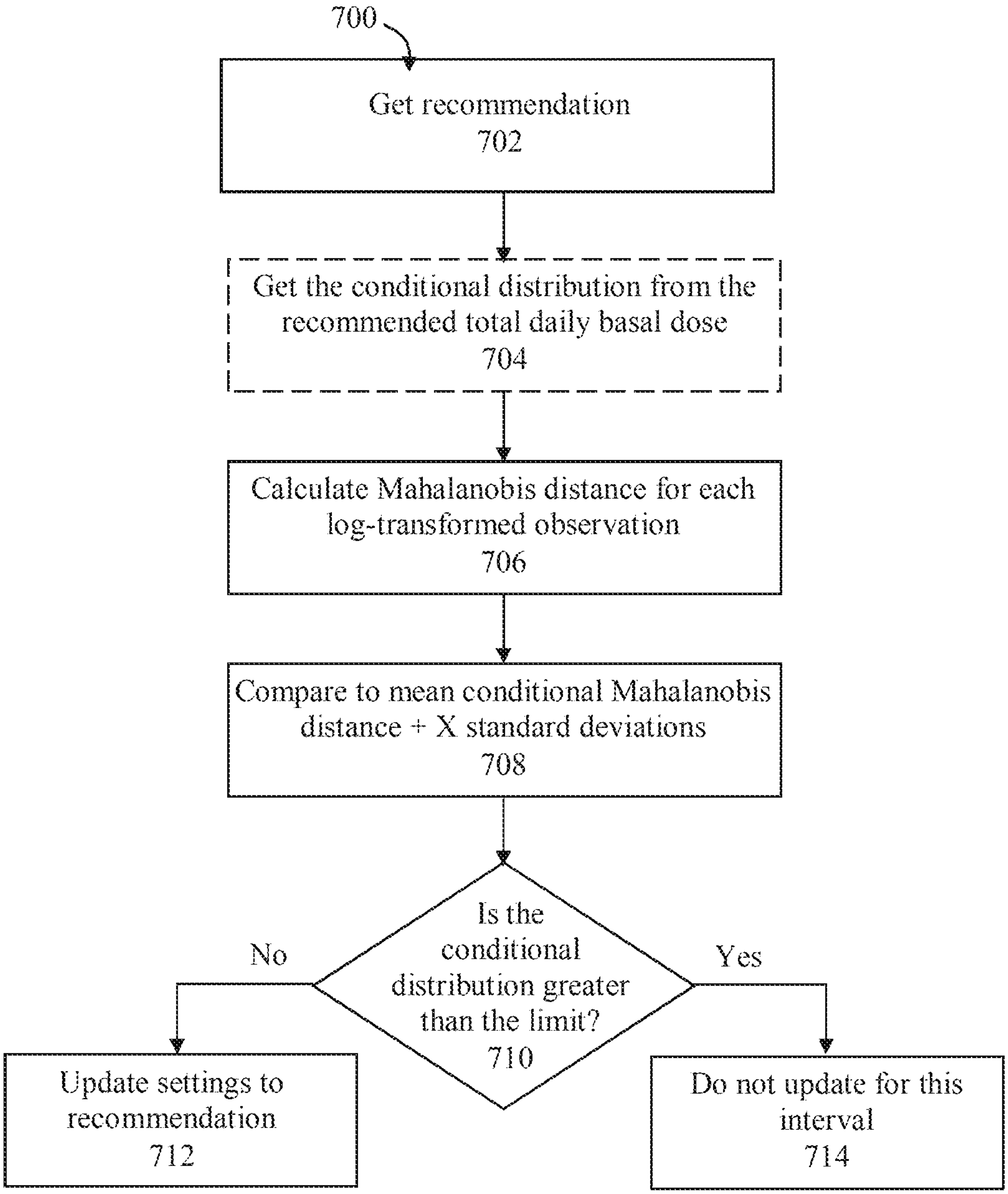
FIG. 10 is a flowchart of a method for applying the constraint generated by the method of FIG. 9, according to an embodiment.

Referring to FIG. 10, a flowchart of a method 700 for applying the constraint generated by method 600 is depicted, according to an embodiment.

At 702, the recommended TDBD is determined. For example, the recommended TDBP can be received, calculated, or otherwise determined as described herein.

At 704, the conditional distribution is determined from the recommended total daily basal dose. For example, $\mathcal{N}$ (CR, ISF|TDBD) is calculated using the recommended TDBD. In certain embodiments, 704 is conditional. In embodiments, 704 can be run each iteration of method 700.

At 706, a Mahalanobis distance is calculated for each log-transformed observation. For example, the Mahalanobis distance can be calculated for log-transformed CR and ISF to the instant distribution.

At 708, a comparison is made to the mean conditional Mahalanobis distance plus a certain X number of standard deviations (e.g., output from method 600). In an embodiment, the CR and ISF are constrained to be within 3 standard deviations of the most likely values given the current estimate for TDBD.

At 710, the Mahalanobis distance from the recommended CR and ISF to the distribution is calculated and is compared to the Mahalanobis distance limit. If the recommendation Mahalanobis distance satisfies (e.g., less than or equal to) the Mahalanobis distance limit, the recommendation is included such that the settings are updated at 712. If the recommendation Mahalanobis distance exceeds the Mahalanobis distance limit, the recommendation is rejected at 714, and the tool returns "no recommendation."

In embodiments, a multi-output neural network can be implemented such that the outputs are the mismatch (as a ratio) between current and "optimal" basal rate, CR, and ISF. The "features" of the model can be parameters of the probability distributions used in the algorithm embodiments described above, as well as any other statistics related to glucose values after meal boluses, correction boluses, during basal only time, aggregate glucose statistics, number of correction boluses, etc. Accordingly, embodiments can provide a one-step change from current to optimal settings, which is advantageous over traditional methods of incremental adjustments offered as recommendations to the HCP.

More particularly, using a neural network, optimal settings can be attained quickly. For example, using extracted features from the patient data, features can be extracted by the machine learning algorithms, such as parameters from distribution in an initialization algorithm (e.g. how frequently the patient goes low, how frequently the patient goes low after meals), which can be fed into the neural network. Outputs from the neural network can be mismatches between a current setting and an optimal setting.

Accordingly, embodiments can be used in a number of different instantiations to more effectively program medical devices.

In an embodiment, such as user inputs long-acting dose, or total daily insulin dose, or weight, and/or age, and diabetes Type in a medical device, such as an insulin pump. A probability distribution using those inputs is used to calculate the most likely CR and ISF and automatically set those values in the pump. Over time, at discrete intervals of time, the settings are automatically adjusted by the adaptation algorithm (which can live in the pump or in the cloud, with settings transmitted to the pump via the mobile app or through direct cellular connection on the pump). If the algorithm is in the cloud, additional data related to exercise and other contextual elements can be used to learn different "profiles" of settings based on context.

In another embodiment, initial settings are provided as an intake form or a calculator to be used by a HCP.

In another embodiment, a settings adaptation algorithm can provide recommendations with explanations in a web-based platform accessible by a user such as a HCP or PWD.

In another embodiment, a HCP can approve recommended settings. In another embodiment, a HCP can just have visible the changes to settings.

In another embodiment, a HCP can set constraints on how much the algorithm can adjust settings on its own.

In another embodiment, systems and methods described herein are applicable for PWD on multiple daily injections using a connected pen that records meal and correction doses.

Figure 11:
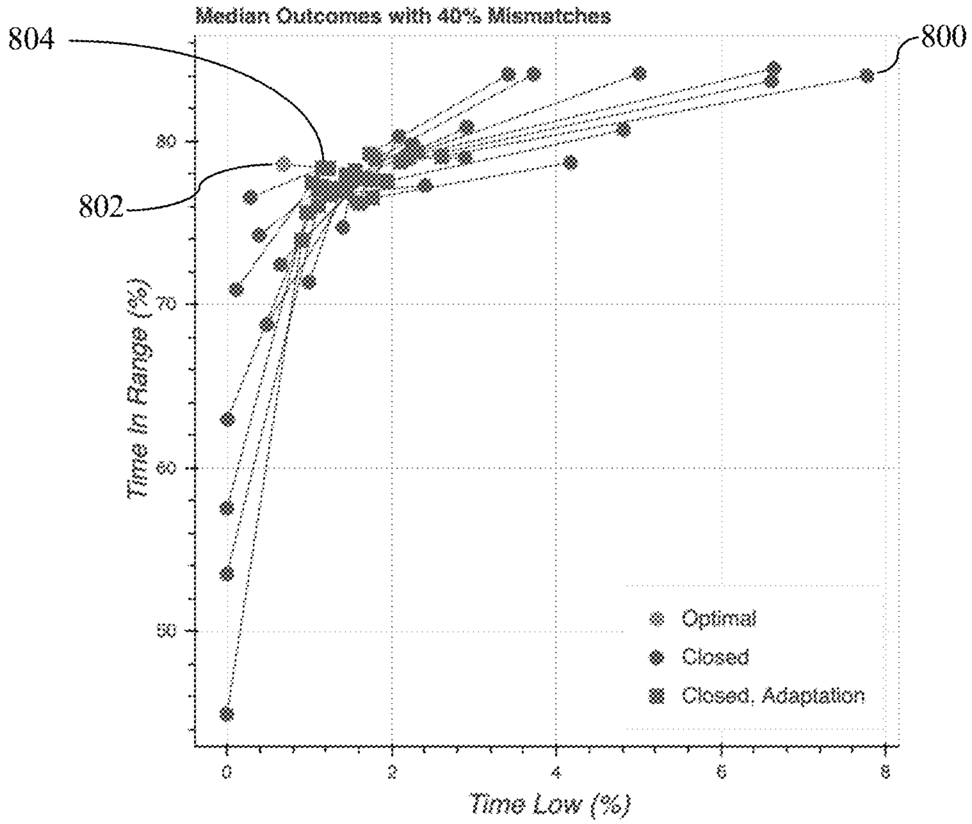
FIG. 11 is a graph of simulation results for embodiments of managing medical device settings described herein, according to embodiments.

The following simulation results emphasize the improvements over traditional systems and methods. Referring to FIG. 11, a graph of simulation results for embodiments of managing medical device settings described herein is depicted, according to embodiments. In particular, traditional closed-loop operation 800 is depicted against closed-loop adaptive 804 in view of optimal (physiology and what is programmed in the medical device have no errors) at 802 Note that the adaptive algorithm instances converge at a point close to optimal compared to instances without adaptive algorithms.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein.

Also incorporated herein by reference in their entirety are commonly owned U.S. Pat. Nos. 6,999,854; 8,133,197; 8,287,495; 8,408,421 8,448,824; 8,573,027; 8,650,937; 8,986,523; 9,173,998; 9,180,242; 9,180,243; 9,238,100; 9,242,043; 9,335,910; 9,381,271; 9,421,329; 9,486,171; 9,486,571; 9,492,608; 9,503,526; 9,555,186; 9,565,718; 9,603,995; 9,669,160; 9,715,327; 9,737,656; 9,750,871; 9,867,937; 9,867,953; 9,940,441; 9,993,595; 10,016,561; 10,201,656; 10,279,105; 10,279,106; 10,279,107; 10,357,603; 10,357,606; 10,492,141; 10,541,987; 10,569,016; 10,736,037; 10,888,655; 10,994,077; 11,116,901; 11,224,693; 11,291,763; and 11,305,057 and commonly owned U.S. Patent Publication Nos. 2009/0287180; 2012/0123230; 2013/0053816; 2014/0276423; 2014/0276569; 2014/0276570; 2018/0071454; 2019/0240398; 2019/0307952; 2020/0206420; 2020/0261649; 2020/0329433; 2020/0368430; 2020/0372995; 2021/0001044; 2021/0113766; 2021/0154405; 2021/0353857; 2022/0062553; 2022/0139522; 2022/0223250; 2022/0233772; 2022/0233773; and 2022/0238201 and commonly owned U.S. patent application Ser. Nos. 17/368,968; 17/677,621; 17/729,464; 17/732,208; 17/878,681; 17/879,959; and Ser. No. 17/886,998.

For purposes of interpreting the claims, it is expressly intended that the provisions of 35 U.S.C. § 112(f) are not to be invoked unless the specific terms "means for" or "step for" are recited in a claim.

The invention claimed is:

1. A system for programming a medical device, comprising:

computing hardware of at least one processor and a memory operably coupled to the at least one processor; and instructions that, when executing on the computing hardware, cause the computing hardware to:

receive at least one parameter from a user of the medical device, retrieve data from a patient population database, the patient population database including existing medical device settings and respective outcomes of the existing medical device settings for existing other patients, fit at least one distribution to the data from the patient population database, select a plurality of likely device settings based on the at least one distribution, and program the medical device with programmed medical device settings using the received at least one parameter and the plurality of likely device settings.

2. The system of claim 1, wherein the at least one distribution is a multivariate log normal distribution.

3. The system of claim 1, wherein the plurality of likely device settings includes a TDI, daily basal requirement, a carb ratio (CR), and an insulin sensitivity factor (ISF).

4. The system of claim 1, wherein the instructions further cause the computing hardware to:

determine whether an adjustment interval has been reached;

when the adjustment interval has been reached, determine an adjustment to at least one of the programmed medical device settings as adjusted medical device settings; and program the medical device with the adjusted medical device settings.

5. The system of claim 4, wherein determining the adjustment to the at least one of the programmed medical device settings comprises:

retrieving operational data for the medical device for a review period, the review period based on a most recent change to the at least one of the programmed medical device settings;

segmenting the operational data for the medical device for the review period into a plurality of influential settings;

calculating a mismatch for at least one of the plurality of influential settings based on at least one distribution from the patient population database;

adjusting the at least one of the plurality of influential settings when the probability of the at least one of the plurality of influential settings is outside of a mismatch range as an adjusted at least one of the plurality of influential settings;

constraining the adjusted at least one of the plurality of influential settings; and determining the adjusted medical device settings based on the constraining.

6. The system of claim 1, wherein the medical device is an ambulatory infusion pump.

7. The system of claim 1, wherein the respective outcomes of the existing medical device settings for existing other patients comprise glycemic outcomes.

8. The system of claim 7, wherein the at least one distribution compares target glycemic outcomes to actual glycemic outcomes.

9. A method for adapting medical device settings for a medical device, the method comprising:

retrieving operational data for a medical device for a review period, the review period based on a most recent change to at least one of the medical device settings;

segmenting the operational data for the medical device for the review period into a plurality of influential settings;

calculating a mismatch for at least one of the plurality of influential settings based on at least one distribution from a patient population database, the patient population database including existing medical device settings and respective outcomes of the existing medical device settings for existing other patients;

adjusting the at least one of the plurality of influential settings when the probability of the at least one of the plurality of influential settings is outside of a mismatch range as an adjusted at least one of the plurality of influential settings;

constraining the adjusted at least one of the plurality of influential settings; and determining the adjusted medical device settings based on the constraining.

10. The method of claim 9, wherein constraining the adjusted at least one of the plurality of influential settings comprises restricting the adjusted at least one of the plurality of influential settings to +−5% of the respective setting.

11. The method of claim 9, wherein segmenting the operational data for the medical device comprises separating basal glucose data and post-meal glucose data.

12. The method of claim 11, wherein for basal glucose data, adjusting the at least one of the plurality of influential settings comprises adjusting a basal rate (BR) when the probability of glucose is outside of a mismatch range for basal rate.

13. The method of claim 12, wherein for post-meal glucose data, adjusting the at least one of the plurality of influential settings comprises adjusting a carb ratio (CR) when the probability of glucose is outside of a mismatch range for carb ratio.

14. The method of claim 13, further comprising:

determining a mismatch for insulin sensitivity factor (ISF) based on the adjusted BR and the adjusted CR; and determining a most likely ISF setting based on at least one distribution;

constraining the most likely ISF setting; and determining an adjusted ISF setting based on the constraining.

15. The method of claim 9, wherein the medical device is an ambulatory infusion pump.

16. The method of claim 9, wherein the respective outcomes of the existing medical device settings for existing other patients comprise glycemic outcomes.

17. The method of claim 16, wherein the at least one distribution compares target glycemic outcomes to actual glycemic outcomes.

* * * * *